(12) United States Patent
Sakuma (10) Patent No.: US 9,696,568 B2
(45) Date of Patent: Jul. 4, 2017

(54) LIGHT SOURCE APPARATUS AND INSPECTION APPARATUS

(71) Applicant: Lasertec Corporation, Yokohama, Kanagawa (JP)

(72) Inventor: Jun Sakuma, Yokohama (JP)

(73) Assignee: Lasertec Corporation, Yokohama, Kanagawa (JP)

( * ) Notice: Subject to any disclaimer, the term of this patent is extended or adjusted under 35 U.S.C. 154(b) by 0 days.

(21) Appl. No.: 15/153,569

(22) Filed: May 12, 2016

(65) Prior Publication Data

US 2016/0334652 A1   Nov. 17, 2016

(30) Foreign Application Priority Data

May 13, 2015   (JP) ................. 2015-097854

(51) Int. Cl.
*G02F 1/11* (2006.01)
*G02F 1/35* (2006.01)
(Continued)

(52) U.S. Cl.
CPC ............ *G02F 1/113* (2013.01); *G01J 1/0407* (2013.01); *G01N 21/9501* (2013.01);
(Continued)

(58) Field of Classification Search
CPC . G02F 1/00; G02F 1/113; G02F 1/116; G02F 1/3534; G02F 1/3551;
(Continued)

(56) References Cited

U.S. PATENT DOCUMENTS 6,894,826 B2 * 5/2005 Doi ................ B23K 26/0604
359/326
7,535,617 B2 * 5/2009 Gupta ................ G01J 3/02
359/285
(Continued)

FOREIGN PATENT DOCUMENTS

JP   H0894338 A    4/1996
JP   2005025054 A  1/2005
(Continued)

OTHER PUBLICATIONS

Japanese Patent Office, Office Action Issued in Japanese Patent Application No. 2015-097854, Jan. 26, 2016, 12 pages.
(Continued)

*Primary Examiner* — Loha Ben
(74) *Attorney, Agent, or Firm* — McCoy Russell LLP (57) ABSTRACT

Provided are a light source apparatus and an inspection apparatus that can stably output a wavelength converted light beam. A light source apparatus includes a laser light source that generates a first fundamental light beam, at least one nonlinear optical crystal that generates a wavelength converted light beam using the fundamental light beam or a harmonic laser beam of the fundamental light beam as an incident light beam, a detector that detects the wavelength converted light beam, an acousto-optic modulator that is disposed in an optical path of the incident light beam in such a way that a zero-order light beam enters the nonlinear optical crystal, and a controller that controls an output intensity of the wavelength converted light beam according to a detection signal from the detector.

6 Claims, 9 Drawing Sheets

(51) Int. Cl.
*H01S 3/00* (2006.01)
*G02F 1/355* (2006.01)
*G02B 27/14* (2006.01)
*G01N 21/95* (2006.01)
*G01J 1/04* (2006.01)
*G01J 3/12* (2006.01)
*G01N 21/17* (2006.01)
*G01N 21/63* (2006.01)

(52) U.S. Cl.
CPC ............ *G02B 27/141* (2013.01); *G02F 1/116* (2013.01); *G02F 1/3534* (2013.01); *G02F 1/3551* (2013.01); *H01S 3/005* (2013.01); *H01S 3/0085* (2013.01); *H01S 3/0092* (2013.01); *G01J 3/1256* (2013.01); *G01N 21/1702* (2013.01); *G01N 21/636* (2013.01); *G01N 2201/068* (2013.01); *G01N 2201/06113* (2013.01)

(58) Field of Classification Search
CPC ... G02B 27/1086; G02B 27/141; H01S 3/005; H01S 3/0085; H01S 3/0092; H01S 3/06754; H01S 3/1068; H01S 5/0687; G01J 1/0407; G01J 3/02; G01J 3/0224; G01J 3/1256; G01N 21/1702; G01N 21/636; G01N 21/9501; G01N 2201/06113; G01N 2201/068
USPC .... 359/285–287, 326, 328, 329, 331; 372/9, 372/13, 25, 26, 28, 30, 33
See application file for complete search history.

(56) References Cited

U.S. PATENT DOCUMENTS

| | | | | |
|---|---|---|---|---|
| 7,606,274 | B2 * | 10/2009 | Mirov | ............ C30B 31/00 372/10 |
| 8,233,508 | B2 * | 7/2012 | Mirov | ............ C30B 31/00 356/437 |
| 8,369,367 | B1 * | 2/2013 | Gao | ............ H01S 5/0687 359/285 |
| 8,831,050 | B2 * | 9/2014 | Gao | ............ H01S 3/1068 359/285 |
| 9,158,177 | B2 * | 10/2015 | Clowes | ............ G02F 1/365 |
| 2011/0220815 | A1 | 9/2011 | Sakuma et al. | |
| 2012/0026578 | A1 | 2/2012 | Sakuma | |

FOREIGN PATENT DOCUMENTS

| | | |
|---|---|---|
| JP | 2005197508 A | 7/2005 |
| JP | 2007206452 A | 8/2007 |
| JP | 4654424 B2 | 3/2011 |
| JP | 2011215472 A | 10/2011 |
| JP | 2014215577 A | 11/2014 |

OTHER PUBLICATIONS

Japanese Patent Office, Office Action Issued in Japanese Patent Application No. 2015-097854, Apr. 26, 2016, 5 pages.

* cited by examiner

LIGHT SOURCE APPARATUS AND INSPECTION APPARATUS

INCORPORATION BY REFERENCE

This application is based upon and claims the benefit of priority from Japanese patent application No. 2015-097854, filed on May 13, 2015, the disclosure of which is incorporated herein in its entirety by reference.

BACKGROUND OF THE INVENTION

1. Field of the Invention

The present invention relates to a light source apparatus and an inspection apparatus.

2. Description of Related Art

In the manufacturing process of a photomask for semiconductor exposure, for which a fine processing is required, it is necessary to inspect microscopic defects that may be contained in the photomask. Further, in the case of a reticle on which a fine exposure pattern is written, an inspection must be performed to check as to whether the actual pattern is written correctly and whether there are any defects in the pattern.

For such purposes, a semiconductor defect inspection apparatus that illuminates the object under inspection with continuous or high repetition pulsed light and detects a change in a light intensity due to scattering or the like for comparison is used. Such semiconductor defect inspection apparatus is available in a variety of types, but regardless of the type, the resolution generally increases as the wavelength of the light source is made shorter. Accordingly, the light source apparatus of the type that produces inspection light in the deep ultraviolet region of the spectrum by wavelength conversion of laser beams using nonlinear optical crystals has come into wide use in recent years. As a principle of the apparatus that detects a change in a light intensity, a light source output needs to be always stable in both the short term and the long term, and thus there have been various methods to control the light source output so as to stabilize it.

Japanese Patent No. 4654424 discloses a light source apparatus that generates light at 213 nm or 266 nm using nonlinear optical crystals. The light source apparatus disclosed in Japanese Patent No. 4654424 uses an element, as means for stabilizing an ultraviolet light output, that changes a refractive index of a fundamental light beam by a photoelastic effect or an electro-optical effect. To be more specific, polarizing adjusting means using the electro-optical effect is disposed in an optical path of an incident light beam entering a nonlinear optical crystal.

Japanese Unexamined Patent Application Publication No. 2005-25054 discloses an apparatus that measures a portion of laser beam and provides feedback control on an acousto-optical element (AO element). More specifically, a first-order diffracted light beam of the AO element is used as an output light beam.

In the technique disclosed in Japanese Patent No. 4654424, as a voltage or pressure is continuously applied to an electro-optical element, which is the polarization adjusting means, the polarization adjusting means could be easily degraded and destroyed, and a performance thereof could be readily reduced. Additionally, as the element itself is expensive, frequent exchange of it will lead to an increase in the cost.

Japanese Unexamined Patent Application Publication No. 2005-25054 discloses a method for controlling and stabilizing an output by the AO element. However, when a zero-order light beam with a small loss is used, a beam profile is degraded due to diffraction, and a quality of a laser beam changes, thereby degrading the performance. For this reason, a first-order diffracted light beam is used as an output light beam. In most cases, as an efficiency of the first-order diffracted light beam is limited to about 0 to 80% of an amount of an incident light beam, a maximum output is reduced by 20% with respect to an input light beam. When a wavelength of such a light beam is converted, a conversion efficiency is further reduced. Further, as the first-order diffracted light beam is output with an angle (twice as great as the Bragg angle) with respect to the incident light beam, it is inconvenient to implement this method. Also, with a short wavelength, materials of the AO element are limited, thereby greatly reducing a diffraction efficiency.

The present invention has been made in light of such circumstances, and an object of the present invention is to provide a light source apparatus having a simple configuration that can stably generate wavelength converted light beams without greatly reducing a generated output and an inspection apparatus having a simple configuration.

SUMMARY OF THE INVENTION

In an exemplary aspect of the present invention, a light source apparatus includes: a laser light source that generates a fundamental light beam, at least one nonlinear optical crystal that generates a wavelength converted light beam using the fundamental light beam or a harmonic laser beam of the fundamental light beam as an incident light beam; a detector that detects the wavelength converted light beam; an acousto-optic modulator that is disposed in an optical path of the incident light beam in such a way that a zero-order light beam enters the nonlinear optical crystal, and controlling means for controlling an output intensity of the wavelength converted light beam according to a detection signal from the detector. With such a configuration, wavelength converted light beams can be stably output.

In the above light source apparatus, the nonlinear optical crystal may generate a deep ultraviolet light with a wavelength in a range of 190 to 220 nm, and the AO modulator may be disposed in at least one of optical paths of two incident light beams that enter the nonlinear optical crystal. Then, wavelength converted light beams in an ultraviolet region can be stably output.

The above light source apparatus may be configured to allow an incident light beam with a wavelength in a range of 1000 to 1200 nm and an incident light beam with a wavelength in a range of 230 to 240 nm to enter the nonlinear optical crystal. Then, wavelength converted light beams in an ultraviolet region can be stably output.

In the above light source apparatus, the acousto-optic modulator may be disposed in an optical path of the incident light beam with the wavelength in the range of 230 to 240 nm.

The AO modulator may be configured to allow transmitted light to enter or be output at the Brewster's angle or an anti-reflective coating may be applied to the AO modulator. Then, incident light beams can be used with almost no loss.

In another exemplary aspect of the present invention, a light source apparatus includes: a first laser light source that generates a first fundamental light beam; a second laser light source that generates a second fundamental light beam, in which the second fundamental light beam has a wavelength different from that of the first fundamental light beam; an at least one nonlinear optical crystal that generates a wavelength converted light beam by sum-frequency mixing that accepts a harmonic laser beam of the second fundamental light beam and the first fundamental light beam as incident light beams; a detector that detects the wavelength converted light beam; an acousto-optic modulator that is disposed in an optical path between the first laser light source and the nonlinear optical crystal or an optical path between the second laser light source and the nonlinear optical crystal, in which the acousto-optic modulator is disposed in such a way that a zero-order light beam enters the nonlinear optical crystal; and control means for controlling an output intensity of the wavelength converted light beam according to a detection signal from the detector. Then, wavelength converted light beams can be stably output.

In the above light source apparatus, a wavelength of the first fundamental light beam may be in a range of 1000 to 1200 nm, an incident light beam with a wavelength in a range of 200 to 280 nm by forth-order or fifth-order harmonic generation of the second fundamental light beam may enter the nonlinear optical crystal, and the acousto-optic modulator may be disposed in an optical path of the first fundamental light beam, an optical path of the second fundamental light beam, or an optical path of a second harmonic light of the second fundamental light beam. Then, wavelength converted light beams in an ultraviolet region can be stably output.

In another exemplary aspect of the present invention, an inspection apparatus may include: the above light source apparatus; and means for reducing coherence in an optical path of the wavelength converted light beam. Thus, stable inspections can be performed.

Moreover, in the light source apparatus, the detector detects a wavelength converted light output that has passed through the means for reducing coherence. Then, stable inspections can be performed.

According to the present invention, it is possible to provide a light source apparatus having a simple configuration and that can stably generate wavelength converted light beams and an inspection apparatus having a simple configuration.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

A light source apparatus according to each of exemplary embodiments generates wavelength converted light beams by, for example, a wavelength conversion element. In the exemplary embodiments, although a light source apparatus that is used as an illumination source of a semiconductor inspection apparatus for inspecting masks and the like will be described, applications of the light source apparatus are not limited to an inspection apparatus.

First Exemplary Embodiment

Figure 1:
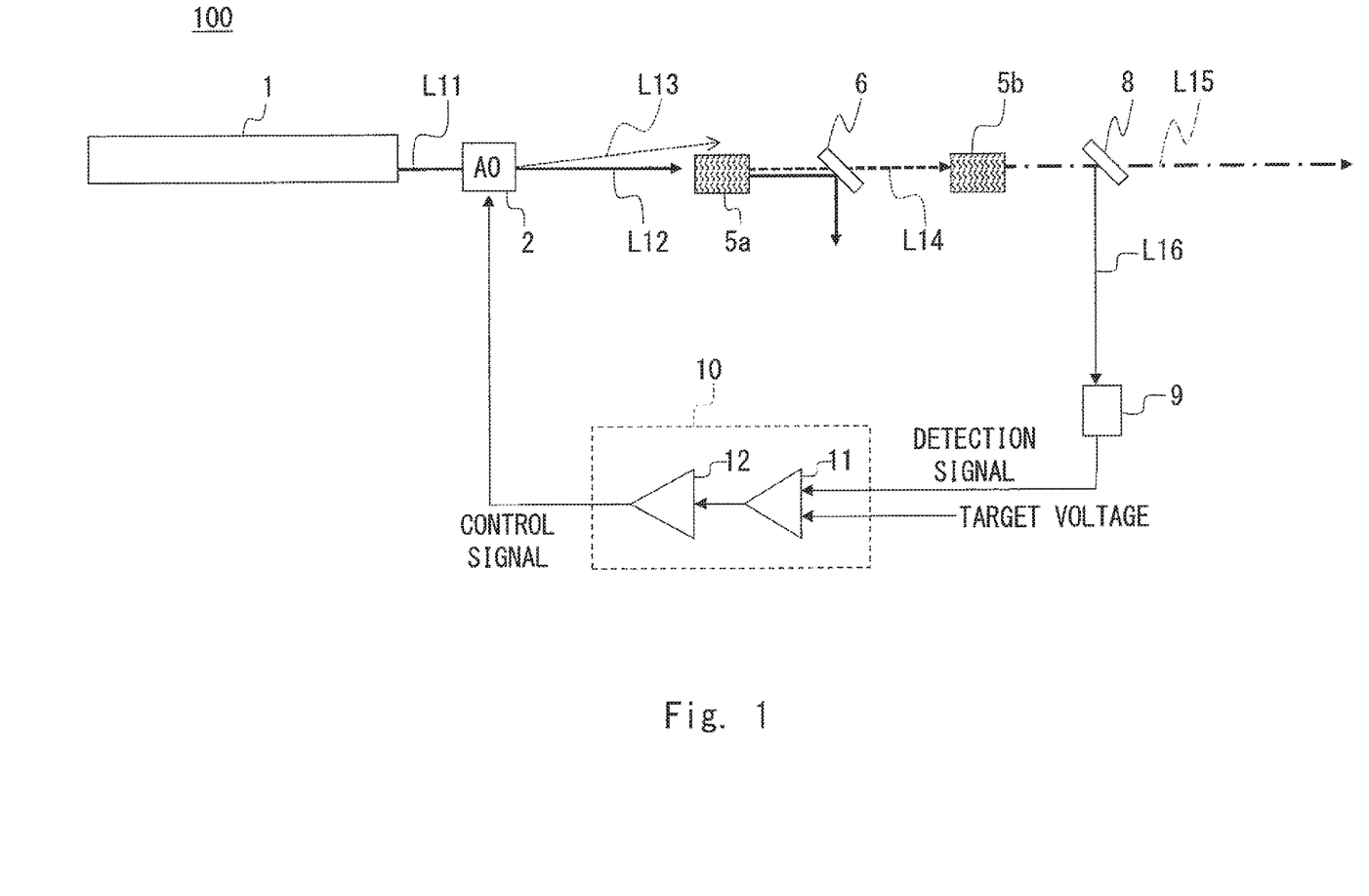
FIG. 1 is a drawing showing a configuration of a light source apparatus according to a first exemplary embodiment.

A light source apparatus 100 according to a first exemplary embodiment will be described by referring to FIG. 1. FIG. 1 is a drawing showing a configuration of the light source apparatus 100. The light source apparatus 100 includes a laser light source 1, an AO modulator 2, a nonlinear optical crystal 5a, a nonlinear optical crystal 5b, a dichroic mirror 6, a sampling mirror 8, a detector 9, and a controller 10.

The laser light source 1 generates a fundamental light beam L11. For example, the laser light source 1 is an Nd:YVO$_4$ laser and generates a laser beam of 1064 nm wavelength as the fundamental light beam L11. The fundamental light beam L11 enters the AO modulator 2.

The AO (Acousto-Optic) modulator 2 is an acousto-optic modulator that modulates an intensity of the fundamental light beam L11 according to a control signal from the controller 10. The AO modulator 2 contains, for example, synthetic quartz. The controller 10 outputs a radio frequency (RF) signal to the AO modulator 2 as the control signal. A piezoelectric element of the AO modulator 2 is oscillated by this radio frequency signal. The oscillation causes compressional waves to be generated inside the acousto-optic element, and thus a diffraction grating is created. An intensity and an angle of a diffracted light beam change according to a change in an intensity and a frequency of the radio frequency signal applied to the AO modulator 2. Thus, a light intensity of a zero-order light beam L12 can be controlled by changing the intensity of the radio frequency signal applied to the AO modulator 2. For example, when the intensity of the radio frequency signal is increased, a diffracted light intensity becomes greater, and the intensity of the zero-order light beam L12, which is transmitted light, is reduced. Conversely, when the intensity of the radio frequency signal is reduced, the diffracted light intensity is reduced, and the intensity of the zero-order light beam L12 can be set in such a way that almost 100% of the zero-order light beam L12 is transmitted through the AO modulator 2. In this way, an intensity of a zero-order light beam can be continuously changed. The AO modulator 2 may be configured to allow an incident light beam to enter or be output at the Brewster's angle or an anti-reflective coating may be applied to the AO modulator 2. By doing so, the incident light beam can be used with almost no loss.

Then, the zero-order light beam L12 from the AO modulator 2 enters the nonlinear optical crystal 5a. That is, the AO modulator 2 is disposed in an optical path between the laser light source 1 and the nonlinear optical crystal 5a. The AO modulator 2 is disposed in such a way that the zero-order light beam L12 enters the nonlinear optical crystal 5a. In other words, a first-order or higher-order diffracted light beam L13 from the AO modulator 2 will not enter the nonlinear optical crystal 5a.

The nonlinear optical crystal 5a contains, for example, an LBO ($LiB_3O_5$) crystal and generates a second harmonic laser beam as a wavelength converted light beam L14. As a fundamental light beam of the zero-order light beam L12 has a wavelength of 1064 nm, the wavelength converted light beam L14 from the nonlinear optical crystal 5a has a wavelength of 532 nm.

The wavelength converted light beam L14 from the nonlinear optical crystal 5a enters the dichroic mirror 6. The dichroic mirror 6 transmits or reflects light according to a wavelength of the light. The dichroic mirror 6 is provided to remove a residual fundamental light beam. The dichroic mirror 6 transmits the wavelength converted light beam L14 and reflects a residual fundamental light beam.

The wavelength converted light beam L14 that has passed through the dichroic mirror 6 enters the nonlinear optical crystal 5b. The nonlinear optical crystal 5b contains a BBO ($\beta$-$BaB_2O_4$) crystal and generates a second harmonic laser beam of the wavelength converted light beam L14. Accordingly, a wavelength converted light beam L15 from the nonlinear optical crystal 5b is a fourth harmonic laser beam of the fundamental light beam L11. As the fundamental light beam has a wavelength of 1064 nm, the wavelength converted light beam L15 has a wavelength of 266 nm.

The wavelength of the wavelength converted light beam L15 is converted by the nonlinear optical crystal 5b, and then the wavelength converted light beam L15 enters the sampling mirror 8. The sampling mirror 8 extracts a portion of the wavelength converted light beam L15 and reflects it so that it will travel in a direction toward the detector 9. The light extracted by the sampling mirror 8 is referred to as a wavelength converted light beam L16. The sampling mirror 8 is a beam splitter having a reflectance of a few %. Accordingly, the sampling mirror 8 reflects only a portion of the wavelength converted light beam L15 and transmits almost the entire wavelength converted light beam L15. The wavelength converted light beam L15 that has passed through the sampling mirror 8 is used as an output light beam. The wavelength converted light beam L15 that has passed through the sampling mirror 8 is used as, for example, illumination light for inspection.

The wavelength converted light beam L16, which is the portion of the wavelength converted light beam L15 extracted by the sampling mirror 8, enters the detector 9. The detector 9 is a photodetector such as a photodiode and a photomultiplier. The detector 9 detects the sampling light beam L16 with a wavelength of 266 nm. That is, the detector 9 converts an output of the wavelength converted light beam L16 into an electrical signal output. The detector 9 outputs a detection signal according to an intensity of the wavelength converted light beam L16 to the controller 10.

The controller 10 controls an output intensity of the wavelength converted light beam L15 from the sampling mirror 8 according to the detection signal. The controller 10 provides feedback control to stabilize the output intensity of the wavelength converted light beam L15. More specifically, the controller 10 includes two stages of amplifiers 11 and 12. The detection signal from the detector 9 is input to the amplifier 11. Further, a target voltage corresponding to a target value of the output light beam is input to the amplifier 11. The two stages of the amplifiers 11 and 12 amplify a difference between the detection signal and the target voltage. Then, the controller 10 outputs a radio frequency signal amplified by the two stages of the amplifiers 11 and 12 to the AO modulator 2 as the control signal. Thus, the AO modulator 2 operates with the radio frequency signal having am amplitude according to the target voltage. The controller 10 changes the intensity of the radio frequency signal applied to the AO modulator 2 according to the detection signal from the detector 9 and controls the output intensity of the wavelength converted light beam L15.

Then, the output from the detector 9 can be almost equal to the target voltage, an output of the wavelength converted light beam L15 can be substantially constant. As has been described above, according to this exemplary embodiment, it is possible to prevent a long-term fluctuation in the output. The output can be easily controlled by adjusting the target voltage. Further, when the AO modulator 2 is used, accurate control can be achieved with an inexpensive apparatus configuration. As radio frequency power applied to the AO modulator 2 will become relatively low, it is very unlikely that a change in quality or the like of materials of the AO modulator 2 will occur. This exemplary embodiment is thus suitable for applications for which long term stability at a low cost, for example, a semiconductor inspection apparatus and the like, is desired. Further, as the zero-order light beam L12 of the AO modulator 2 is used, when the radio frequency signal intensity is reduced, almost 100% of an output of the zero-order light beam can be transmitted, and a generated ultraviolet light output can be almost maximum.

On the other hand, a wavelength converted light beam output in the case of harmonic generation depends on a square of the fundamental light intensity. It is thus possible to greatly change the output of the wavelength converted light beam with a low diffraction efficiency. For example, when an output of the zero-order light beam L12 is changed by 80 to 100% by the AO modulator 2, theoretically, an output of the wavelength converted light beam L14 can be changed in a range of 64 to 100%. Therefore, control in a greater range of outputs becomes possible. Further, a beam profile of the zero-order light beam changes by controlling the radio frequency power. A conversion efficiency of the nonlinear optical crystal 5a changes by a change in the beam profile or the like. Therefore, when an output of a zero-order light beam is changed by 80 to 100% by the AO modulator 2, in practice, the output of the wavelength converted light beam L14 was controlled in a range of 50 to 100%. In such a case, the output of the wavelength converted light beam L15, which is the fourth harmonic laser beam, will theoretically become 41 to 100%, but was controlled in a range of 20 to 100% in practice.

In this exemplary embodiment, two nonlinear optical crystals 5a and 5b are arranged in the subsequent stages of the AO modulator 2. Accordingly, the output of the fourth harmonic laser beam L15 is substantially proportional to the fourth power of a change in an output of the incident light beam due to diffraction in the AO modulator 2. It is thus possible to further increase an adjusting range of the output. Moreover, by the use of the AO modulator 2, the wavelength converted light beam L15 can be adjusted at a high response speed.

When the zero-order light beam L12 of the AO modulator 2 is used, a maximum output can be increased more than when the first-order diffracted light beam L13 is used. For example, when an efficiency of the first-order diffracted light beam L13 is in a range of 0 to 85%, an output of the second harmonic laser beam will be in a range of 0 to 72.3%, and an output of the wavelength converted light beam L15 will be in a range of 0 to 52%. Accordingly, with such a configuration that allows the zero-order light beam L12 to enter the nonlinear optical crystal 5a, the usage efficiency of the wavelength converted light beam can be improved.

Moreover, as an optical path of the zero-order light beam L12 does not bend, it is easy to implement the configuration that uses the zero-order light beam L12 and to adjust an output. That is, as the zero-order light beam L12 is transmitted light that passes through the AO modulator 2, even when the radio frequency power changes, an emission angle will become constant. On the other hand, when the radio frequency power is adjusted, a diffraction angle of the first-order diffracted light beam L13 changes. Accordingly, if the first-order diffracted light beam L13 is used, an emission angle will change, and it is thus difficult to implement the configuration that uses the first-order diffracted light beam L13 and to adjust an output. In this exemplary embodiment, with such a configuration that allows the zero-order light beam L12 to enter the nonlinear optical crystal 5a, it is possible to easily implement the configuration that uses the zero-order light beam L12 and to easily adjust an output.

When the zero-order light beam of the AO modulator 2 is used, a beam profile is degraded. However, although the zero-order light beam, a beam profile of which has been degraded after passing through the AO modulator 2, reduces an output of the wavelength converted light beam by greater than or equal to a reduction in an output of the zero-order light beam, an influence of the reduction will be filtered in the process of the wavelength conversion. Thus, a profile of the second harmonic laser beam will not be degraded much, and the reduction will have almost no influence on the fourth harmonic laser beam. A beam profile of the wavelength converted light beam L15, which is the fourth harmonic laser beam, is thus favorable. In particular, it has been confirmed in an experiment that when an output is stabilized near the maximum output (a zero-order light beam is in a range of 70 to 100%, and a first-order or higher-order diffracted light beam is in a range of 0 to 30%), a beam quality of the wavelength converted light beam stayed largely the same, thereby not causing a problem in any applications.

In this exemplary embodiment, the AO modulator 2 is disposed in the optical path of the incident light beam that enters the nonlinear optical crystal 5a. That is, as the AO modulator 2 is disposed in the optical path of the fundamental light beam L11 having a long wavelength and low photon energy, it is possible to prevent degradation of the AO modulator 2. For example, if the AO modulator 2 is disposed directly in an optical path of the fourth harmonic laser beam L15, a risk that the AO modulator 2 will be degraded will become higher due to high photon energy. On the other hand, reliability can be improved by disposing the AO modulator 2 in the optical path of the fundamental light beam L11 having a wavelength longer than that of the fourth harmonic laser beam L15.

Second Exemplary Embodiment

Figure 2:
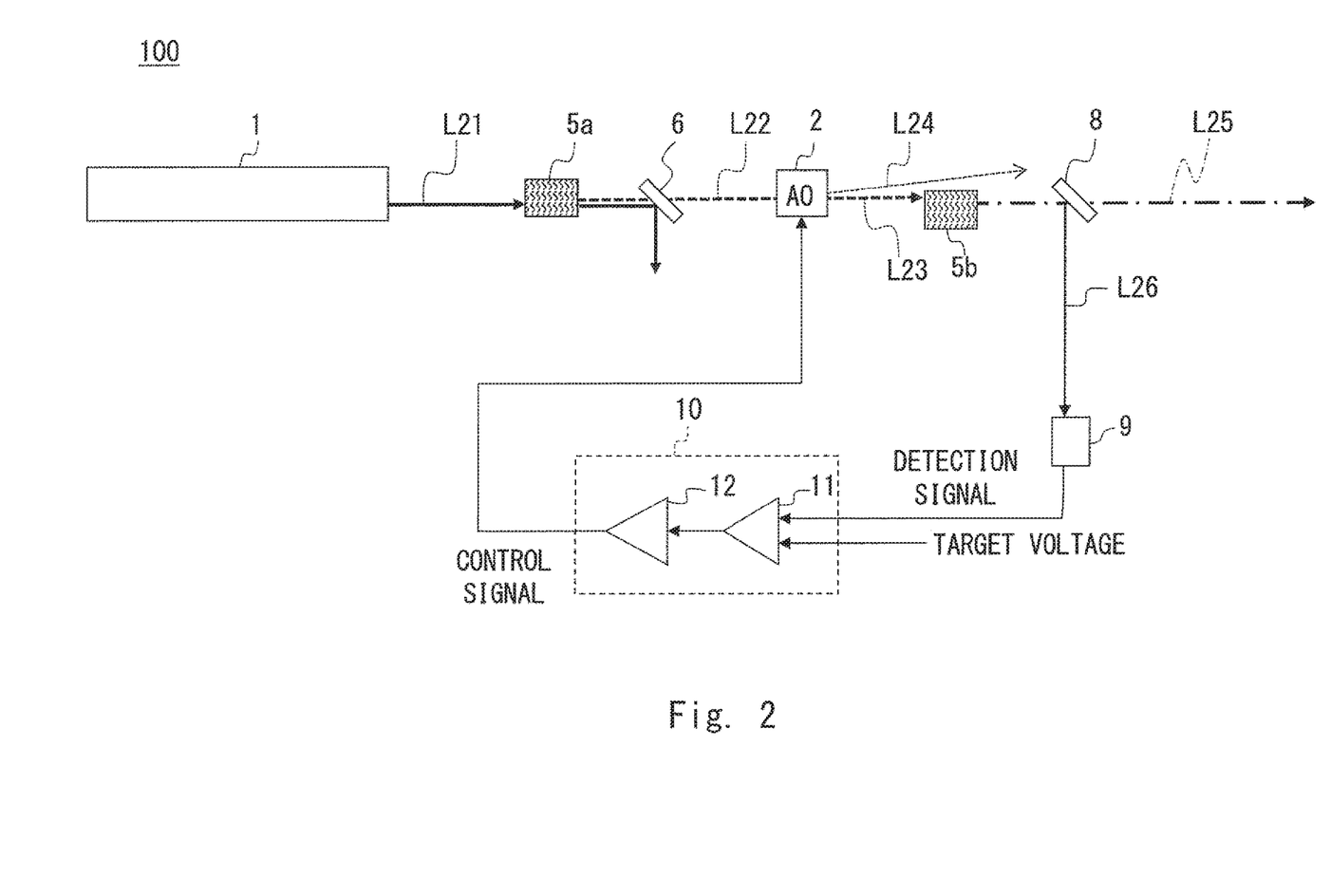
FIG. 2 is a drawing showing a configuration of a light source apparatus according to a second exemplary embodiment.

A configuration of a light source apparatus 100 according to this exemplary embodiment will be described by referring to FIG. 2. FIG. 2 is a drawing showing a configuration of the light source apparatus 100 according to the second exemplary embodiment. A difference between the configuration according to the second exemplary embodiment and the configuration according to the first exemplary embodiment is a position of the AO modulator 2. In the second exemplary embodiment, the AO modulator 2 is disposed in the subsequent stage of the nonlinear optical crystal 5a. To be more specific, the AO modulator 2 is disposed between the dichroic mirror 6 and the nonlinear optical crystal 5b. That is, the AO modulator 2 is disposed in an optical path of a second harmonic laser beam L22 that enters the nonlinear optical crystal 5b. A zero-order light beam L23 of the AO modulator 2 enters the nonlinear optical crystal 5b. Note that the configuration of the second exemplary embodiment is the same as that of the first exemplary embodiment except for the position of the AO modulator 2.

A wavelength of a fundamental light beam L21 from the laser light source 1 is converted by the nonlinear optical crystal 5a, which is an LBO crystal. A second harmonic laser beam generated in the nonlinear optical crystal 5a enters the dichroic mirror 6 as a wavelength converted light beam L22. The dichroic mirror 6 separates the wavelength converted light beam L22 from a residual fundamental light beam.

The wavelength converted light beam L22 that has passed through the dichroic mirror 6 enters the AO modulator 2. The AO modulator 2 generates a first-order diffracted light beam L24 as well as a zero-order light beam L23. A control signal from the controller 10 is input to the AO modulator 2. Thus, an output of the zero-order light beam L23 is controlled by feedback control that is the same as the one described in the first exemplary embodiment. The zero-order light beam L23 enters the nonlinear optical crystal 5b, and the first-order diffracted light beam L24 will not enter the nonlinear optical crystal 5b.

The nonlinear optical crystal 5b is a BBO ($\beta$-BaB$_2$O$_4$) crystal and converts a wavelength of the zero-order light beam L23. Then, a second harmonic laser beam of the zero-order light beam L23, i.e., a fourth harmonic laser beam of the fundamental light beam L21, is generated. The second harmonic laser beam of the zero-order light beam L23 generated in the nonlinear optical crystal 5b enters the sampling mirror 8 as a wavelength converted light beam L25. The sampling mirror 8 extracts a portion of the wavelength converted light beam L25, which will be referred to as a wavelength converted light beam L26. The detector 9 detects the wavelength converted light beam L26.

With such a configuration, almost the same advantages as those of the first exemplary embodiment can be achieved. That is, an output of the wavelength converted light beam L25 can be stabilized. Further, in the configuration according to the second exemplary embodiment, one stage of the nonlinear optical crystal 5b is disposed in the subsequent stage of the AO modulator 2. Accordingly, an output of the wavelength converted light beam L26 is proportional to a square of a change in an output of the incident light beam due to diffraction in the AO modulator 2. It is thus possible to perform accurate control on an output.

Note that in the first and second exemplary embodiments, although it has been described that the fundamental light beams L11 and L21 each have a wavelength of 1064 nm, and the wavelength converted light beams L15 and L25, which are the fourth harmonic laser beams of the fundamental light beams L11 and L21, respectively, and each have a wavelength of 266 nm, are the output light beams, the wavelengths of the fundamental light beams and wavelength converted light beams are not limited to these values. For example, a wavelength of the fundamental light beam may be in a range of 1000 to 1120 nm, and the wavelength converted light beams L15 and L25 may each have a wavelength in a range of 200 to 280 nm in the case of fourth-order or fifth-order harmonic generation of the fundamental light beam. The AO modulator 2 may be applied to any of fundamental light beams in the case of second harmonic generation, fundamental light beams in the case of second, fourth, and fifth harmonic generation, and second-order harmonic laser beams.

Third Exemplary Embodiment

Figure 3:
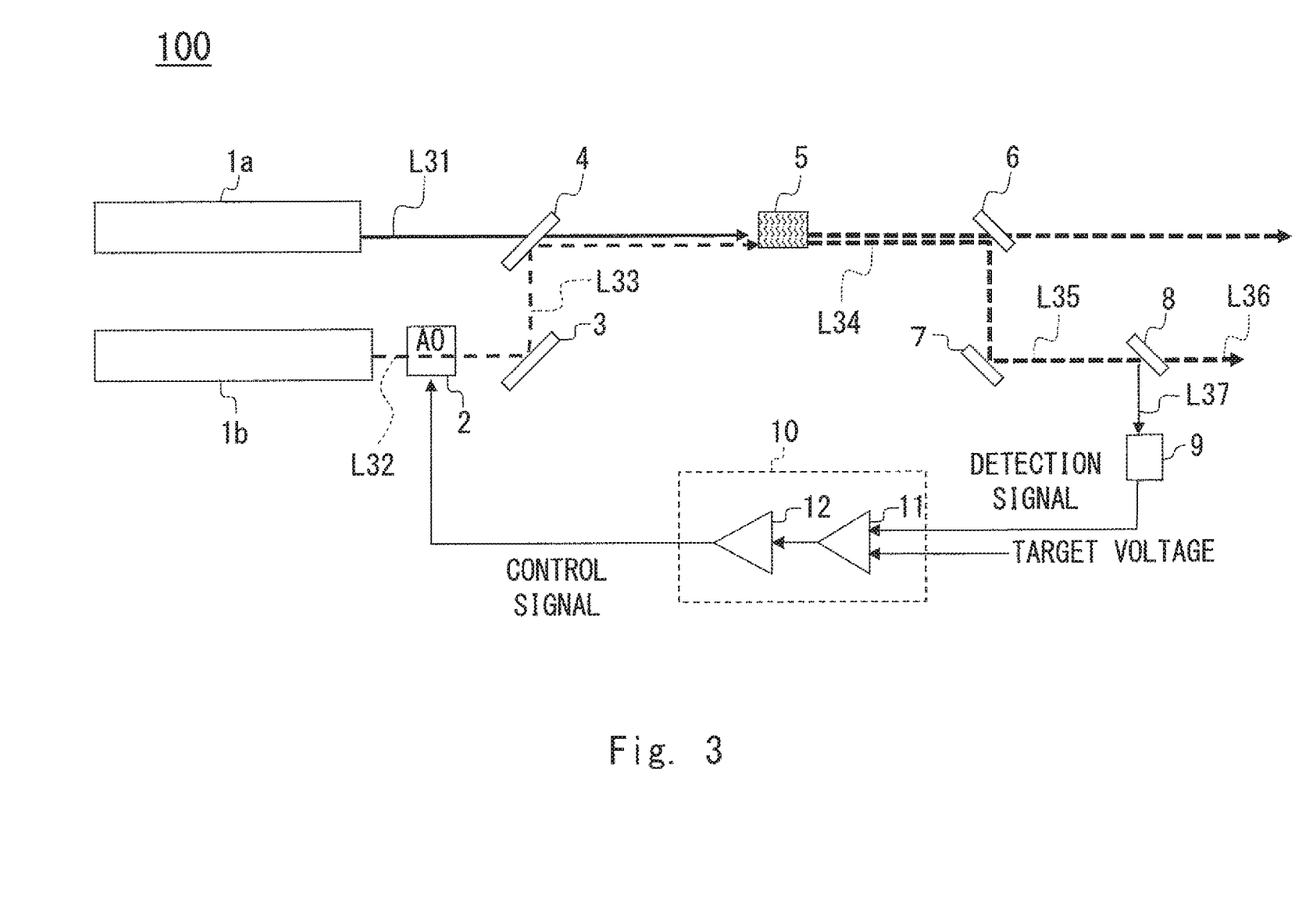
FIG. 3 is a drawing showing a configuration of a light source apparatus according to a third exemplary embodiment.

A configuration of a light source apparatus 100 according to this exemplary embodiment will be described by referring to FIG. 3. FIG. 3 is a drawing showing a configuration of the light source apparatus 100 according to a third exemplary embodiment. In the first and second exemplary embodiments, although it has been described that the wavelength converted light beams L15 and L25 are generated as the wavelength converted light beams by the second harmonic generation in two stages, in this exemplary embodiment, the wavelength converted light beams are generated by sum-frequency mixing. In this exemplary embodiment, for example, an ultraviolet light output having a wavelength in a range of 190 to 220 nm is generated by the sum-frequency mixing. Note that the parts of the descriptions that are common to the description of the first and second exemplary embodiments will be omitted.

In this exemplary embodiment, the light source apparatus 100 includes a laser light source 1*a* and a laser light source 1*b*. The laser light source 1*a* generates, for example, a fundamental light beam L31 with a wavelength of 1100 nm. The laser light source 1*b* generates, for example, a fundamental light beam L32 with a wavelength of 234 nm. The fundamental light beam L31 from the laser light source 1*a* enters a nonlinear optical crystal 5 via a coupling mirror 4.

The fundamental light beam L32 from the laser light source 1*b* enters the AO modulator 2. The AO modulator 2 changes an output intensity of the fundamental light beam L32 in a manner similar to that in the first exemplary embodiment. Note that a first-order diffracted light beam is not shown in FIG. 3. Zero-order light beam L33 of the AO modulator 2 enters the nonlinear optical crystal 5 via the mirror 3 and the coupling mirror 4. The coupling mirror 4 couples the fundamental light beam L31 with the zero-order light beam L33, and then the fundamental light beam L31 and the zero-order light beam L33 become coaxial and propagate. Note that the coupling mirror 4 may be a dichroic mirror that transmits the fundamental light beam L31 with a wavelength of 1100 nm and reflects the zero-order light beam L33 with a wavelength of 234 nm. In this manner, in this exemplary embodiment also, the AO modulator is disposed in an optical path of an incident light beam entering the nonlinear optical crystal 5 so that the zero-order light beam of the AO modulator 2 enters the nonlinear optical crystal 5. Note that in a manner similar to the first and second exemplary embodiment, the first-order diffracted light beam of the AO modulator 2 will not enter the nonlinear optical crystal 5.

The nonlinear optical crystal 5 generates a sum-frequency of the fundamental light beam L31 and the zero-order light beam L33. The nonlinear optical crystal 5 contains, for example a CLBO (CsLiB$_6$O$_{10}$) crystal. A CLBO crystal generates deep ultraviolet light by the sum-frequency mixing using NCPM (Non-critical Phase-matching) or under a condition close to NCPM. As respective wavelengths of the two fundamental light beams are 1100 nm and 234 nm, the nonlinear optical crystal 5 generates a wavelength converted light beam L34 with a wavelength of 193 nm by the sum-frequency mixing. The wavelength converted light beam L34 enters the dichroic mirror 6. The dichroic mirror 6 separates a residual fundamental light beam and a wavelength converted light beam L35 with a wavelength of 193 nm. To be more specific, the dichroic mirror 6 reflects the wavelength converted light beam L35 and transmits the fundamental light beams having the respective wavelengths of 1100 nm and 234 nm.

The wavelength converted light beam L35 that is reflected by the dichroic mirror 6 is reflected by the mirror 7 and enters the sampling mirror 8. The sampling mirror 8 is a beam splitter that splits the incident wavelength converted light beam L35 into a wavelength converted light beam L36 and a wavelength converted light beam L37. The wavelength converted light beam L36 that passed through the sampling mirror 8 is extracted as an output light beam. The detector 9 detects the wavelength converted light beam L37 reflected by the sampling mirror 8. Accordingly, in a manner similar to that in the first exemplary embodiment, in this exemplary embodiment also, the controller 10 controls the AO modulator 2 in such a way that an output of the wavelength converted light beam L36 will become constant.

With such a configuration, the same advantage as that of the first exemplary embodiment can be achieved by this exemplary embodiment. That is, the output of the wavelength converted light beam L36 can be stabilized. Moreover, in the configuration according to the third exemplary embodiment, the nonlinear optical crystal 5 that performs the sum-frequency mixing is disposed in the subsequent stage of the AO modulator 2. Thus, an output of the wavelength converted light beam L34 is substantially proportional to an output change of the zero-order light beam L33 due to diffraction in the AO modulator 2. In practice, a greater output change is possible by degrading of a profile by the AO element.

Note that in the above descriptions, although the AO modulator 2 is disposed in an optical path of the fundamental light beam L32, the AO modulator 2 may be disposed in an optical path of the fundamental light L31. Alternatively, the AO modulators 2 may be disposed in optical paths of both of the laser light sources 1*a* and 1*b*. That is, the AO modulator 2 may be disposed in at least one of the optical paths of two incident light beams that enter the nonlinear optical crystal 5.

A range of control will be greater when the AO modulator 2 is disposed in the optical path of either of the fundamental light beams L31 and L32 than when the AO modulator 2 is directly disposed in the optical path of the wavelength converted light beam L34 with a wavelength of 193 nm. This is because the diffraction frequency will become lower as the wavelength becomes longer, provided that the materials of the AO modulators are the same.

Moreover, directly disposing the AO modulator 2 in the optical path of the wavelength converted light beam L34 with a wavelength of 193 nm increases a risk of degrading the AO modulator 2 by high photon energy. On the other hand, in this exemplary embodiment, as the AO modulator 2 is disposed in the optical path of the fundamental light beam that has a wavelength longer than the wavelength converted light beam with a wavelength of 193 nm, reliability can be improved.

In this exemplary embodiment, the wavelength converted light beam L35 generated in the nonlinear optical crystal 5 is separated by the sampling mirror 8 and measured by the detector 9. As a response speed of the AO modulator 2 is sufficiently high, when the AO modulator 2 is disposed in the optical path of either of the fundamental light beams, the output of the wavelength converted light beam L36, which is the output light beam, can be stabilized. Even when the fundamental light beam L31 on which the AO modulator 2 is not disposed fluctuates, the output can be stabilized.

Figure 4:
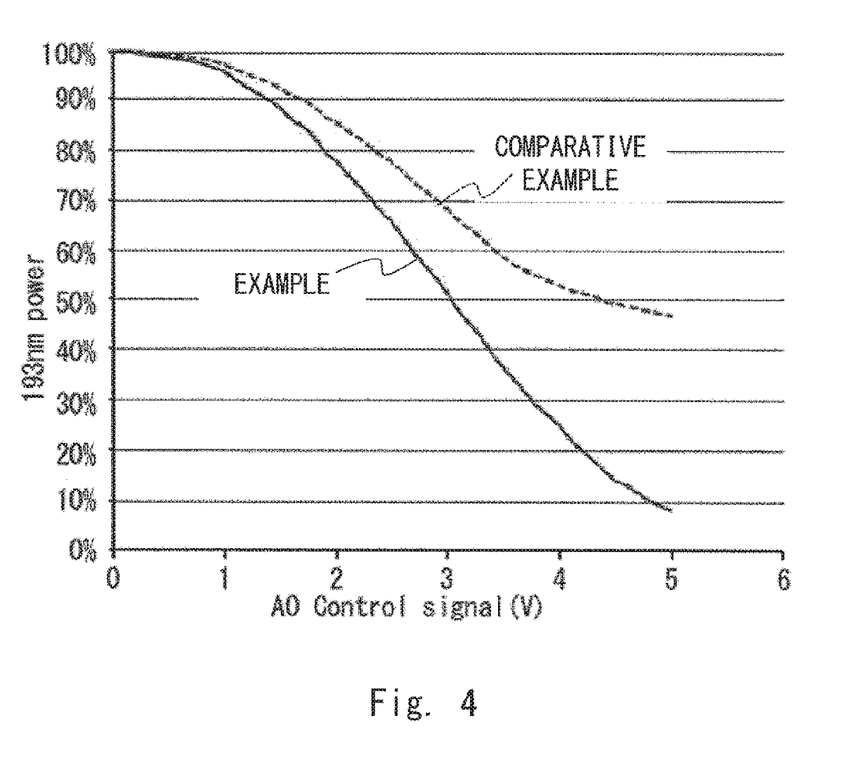
FIG. 4 shows output data of a light beam at 193 nm when an AO modulator is applied to a fundamental light beam.

In an experiment, the AO modulator 2 having a maximum diffraction efficiency of 70% at a wavelength 234 nm was used, and the output of the wavelength converted light beam L36 was smoothly controlled in a range of 10 to 100%. FIG. 4 is a graph showing an output of light at 193 nm in the example shown in FIG. 3 and an output of light at 193 nm in the comparative example. In FIG. 4, the horizontal axis represents a control signal of the AO modulator 2, and the vertical axis represents output power of the wavelength converted light beam. The output of the wavelength converted light beam was adjusted in a range of 10 to 100% by changing the diffraction efficiency of the AO modulator 2 in a range of 50 to 100%. This is considered to be because of an effect of reducing a wavelength conversion efficiency by a change in the beam profile.

On the other hand, in the comparative example, an output of a wavelength converted light beam is shown when the AO modulator 2 is disposed in the optical path of the wavelength converted light beam L36 instead of the optical path of the fundamental light beam L32. In the comparative example, the output of the wavelength converted light beam L36 with a wavelength of 193 nm can be reduced by only about 50%. This is considered to be because the diffraction efficiency will become lower as the wavelength becomes shorter, and because, unlike in the above example according to the third embodiment, a change in the beam profile has no effect.

Figure 5:
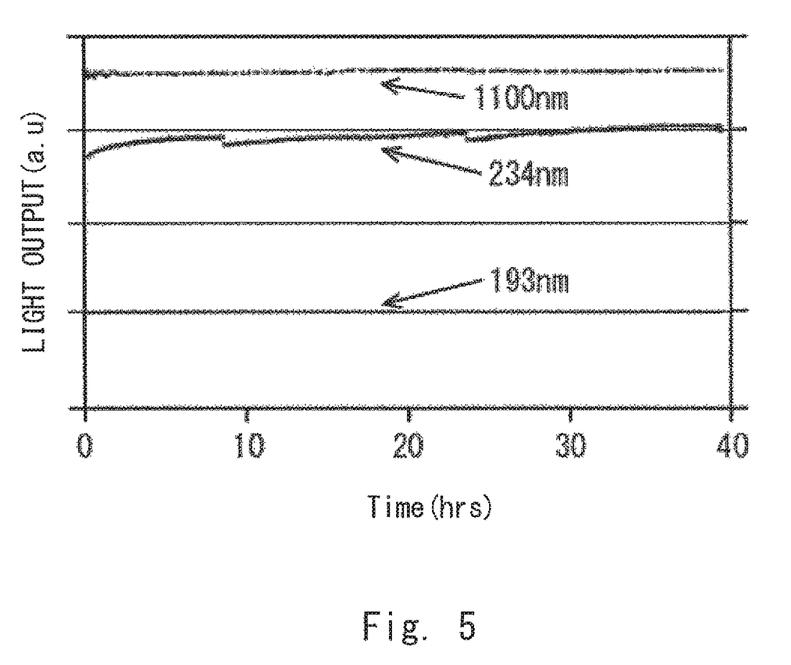
FIG. 5 shows data representing stability when the AO modulator is disposed in an optical path of a light beam at 234 nm.

FIG. 5 shows data when the output of the wavelength converted light beam L36 is stabilized by the configuration shown in FIG. 3. In FIG. 5, the horizontal axis represents a time, and the vertical axis represents light outputs of the fundamental light beam L31 with a wavelength of 1100 nm, the fundamental light L32 with a wavelength of 234 nm, and the wavelength converted light beam L36 with a wavelength of 193 nm. As shown in FIG. 5, the output of the wavelength converted light beam L36 can be stabilized even when the fundamental light beams L31 and L32 fluctuate.

Modified Example

Figure 6:
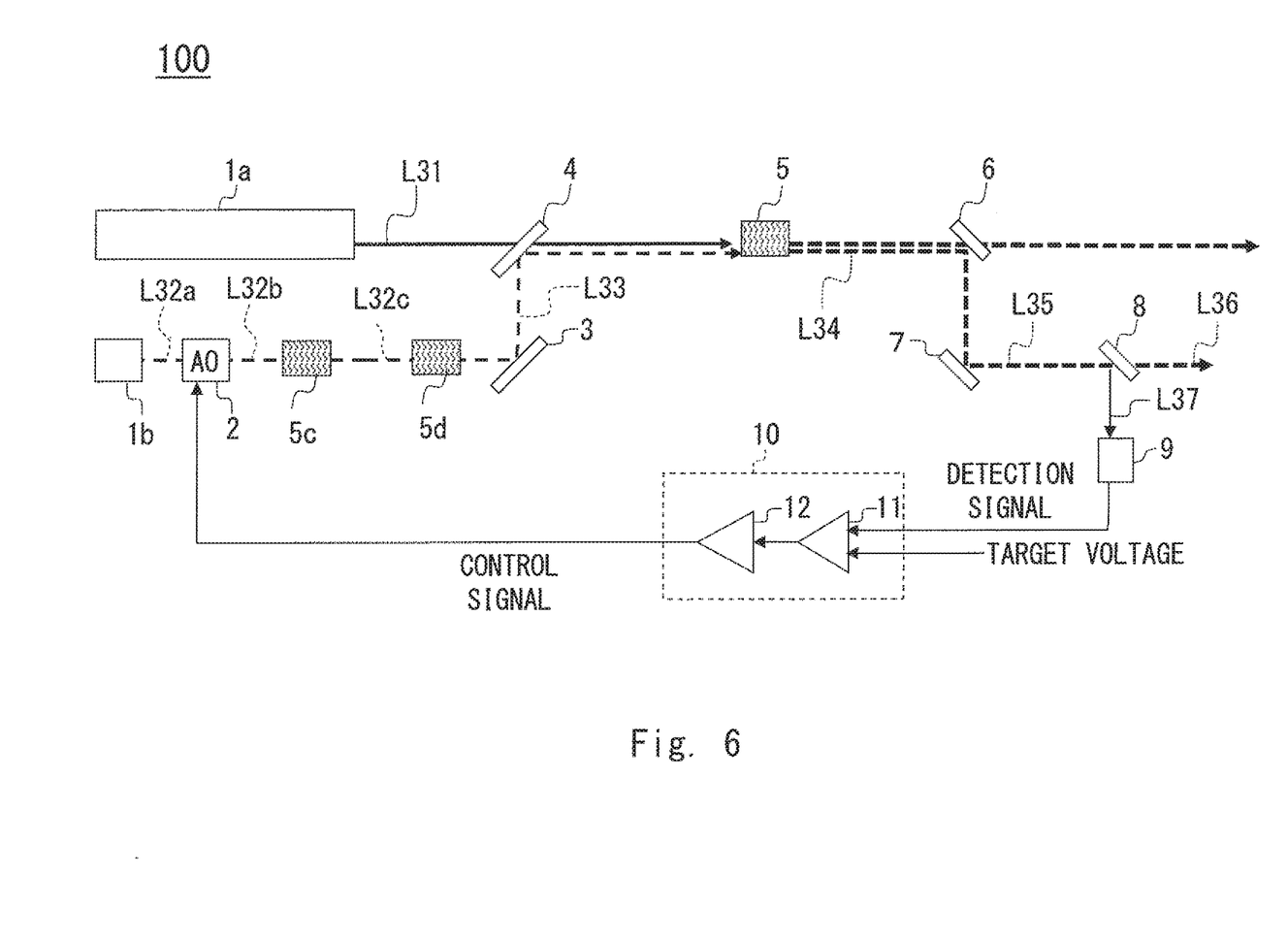
FIG. 6 is a drawing showing a configuration of a light source apparatus according to a modified example of the third exemplary embodiment.

FIG. 6 shows a modified example of the light source apparatus 100 according to the third exemplary embodiment. In this example, a part of a configuration from the laser light source 1b to the mirror 3 is different from that of the light source apparatus 100 shown in FIG. 3. More specifically, in the configuration according to the modified example, the laser light source 1b of FIG. 3 is configured to include nonlinear optical crystals in a manner similar to a configuration shown in FIG. 1 of Japanese Unexamined Patent Application Publication No. 2014-215577. Note that as the other elements shown in FIG. 6 are the same as those of the configuration shown in FIG. 3, descriptions of these other elements according to the modified example will be omitted. For example, as in the configuration shown in FIG. 3, the wavelength converted light beam L34 with a wavelength of 193 nm is generated by the sum-frequency mixing in the nonlinear optical crystal 5.

The laser light source 1b generates a laser beam with a wavelength in a range of 932 to 936 nm as a fundamental light beam L32a. An Optically Pumped Semiconductor Laser (OPSL) that performs photoexcitation by a diode laser or the like using a semiconductor quantum well as a gain medium may be used as the laser light source 1b for generating the fundamental light beam L32a. Alternatively, the laser light source 1b may be a light source such as an External Cavity Diode Laser (ECDL), Distributed Feedback (DFB)/Distributed Bragg Reflector (DBR) laser that use a semiconductor quantum well as a gain medium or a Tapered Amplifier (TA) that is combined with these lasers.

The fundamental light beam L32a enters the AO modulator 2. A zero-order light beam L32b of the AO modulator 2 enters a nonlinear optical crystal 5c such as an LBO or the like. Thus, the nonlinear optical crystal 5c generates a second harmonic laser beam of the zero-order light beam L32b as a wavelength converted light beam L32c. The wavelength converted light beam L32c has a wavelength in a range of 466 to 468 nm.

The wavelength converted light beam L32c enters a nonlinear optical crystal 5d such as a BBO or the like. The nonlinear optical crystal 5d generates a fourth harmonic laser beam of the fundamental light beam L31a as a wavelength converted light beam L33 by second harmonic generation. The wavelength converted light beam L33 has a wavelength in a range of 233 to 234 nm. The wavelength converted light beam L33 and the wavelength converted light beam L31 will be an incident light beam into a wavelength conversion element 5. The wavelength conversion element 5 generates a sum-frequency mixed light beam of the wavelength converted light beam L33 and the wavelength converted light beam L31. Accordingly, as in the configuration shown in FIG. 3, an intensity of the wavelength converted light beam L36 can be controlled. Further, as the three nonlinear optical crystals 5c, 5d, and 5 are arranged in the subsequent stages of the AO modulator 2, a range of control can be increased.

In the light source apparatus 100 that uses the sum-frequency mixing, a position at which the AO modulator 2 is disposed is not particularly limited. The AO modulator 2 may be disposed, for example, between the nonlinear optical crystals 5c and 5d. The AO modulator 2 may be disposed in an optical path from the laser light source 1b to the nonlinear optical crystal 5 that performs the sum-frequency mixing. Alternatively, the AO modulator 2 may be disposed in an optical path from the laser light source 1a to the nonlinear optical crystal 5 that performs the sum-frequency mixing. It is obvious that the AO modulator 2 may be disposed in both the optical path from the laser light source 1b to the nonlinear optical crystal 5 that performs the sum-frequency mixing and the optical path from the laser light source 1a to the nonlinear optical crystal 5 that performs the sum-frequency mixing.

In FIG. 6, although the fourth harmonic laser beam of the fundamental light beam L32a is shown as the light beam incident to the nonlinear optical crystal 5 that performs the sum-frequency mixing, a fifth harmonic laser beam of the fundamental light L32a may be the incident light beam. Thus, the fourth harmonic laser beam or the fifth harmonic laser beam with a wavelength in a range of 200 to 280 nm may enter the nonlinear optical crystal 5. The AO modulator 2 may be disposed in at least one optical path of the first fundamental light beam L31, the second fundamental light beam L32a, and the wavelength converted light beam L32c that is a second harmonic laser beam. In the configurations of FIGS. 3 and 6, the wavelength of the fundamental light beam L31 is preferably in a range of 1000 to 1200 nm.

Fourth Exemplary Embodiment

Figure 7:
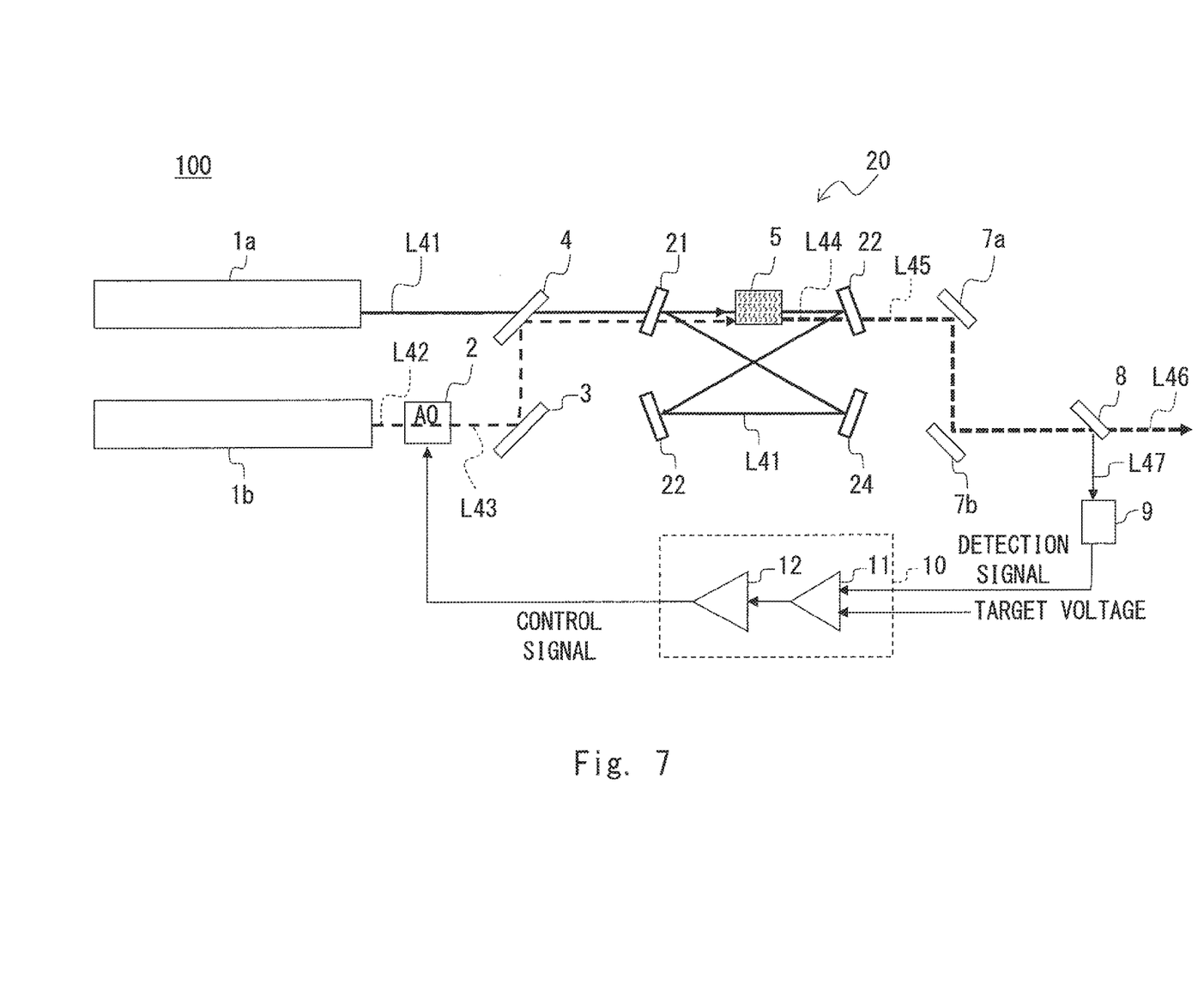
FIG. 7 is a drawing showing a configuration of a light source apparatus according to a fourth exemplary embodiment.

As shown in FIG. 7, in a fourth exemplary embodiment, the light source apparatus 100 is a Continuous Wave (CW) light source that uses single resonant oscillation sum-frequency mixing. Therefore, an external resonator 20 is disposed in the light source apparatus 100. The external resonator 20 includes four optical mirrors 21 to 24. The nonlinear optical crystal 5 is disposed inside the external resonator 20. For example, a configuration shown in FIG. 8 of Japanese Unexamined Patent Application Publication No. 2011-215472 may be used for the single resonant oscillation sum-frequency mixing. Note that as the elements of this configuration other than the external resonator 20 are the same as those of the configuration according to the third exemplary embodiment, descriptions of these other elements of this exemplary embodiment will be omitted as appropriate.

A fundamental light beam L41 with a wavelength of 1100 nm enters the coupling mirror 4. A fundamental light beam L42 with a wavelength of 234 nm enters the AO modulator 2. The AO modulator 2 controls a zero-order light beam intensity in a manner similar to that in the first to third exemplary embodiments. A zero-order light beam L43 from the AO modulator 2 enters the coupling mirror 4 via the mirror 3. The fundamental light beam L41 and the zero-order light beam L43 are made coaxial by the coupling mirror 4, propagate, and then enter the external resonator 20.

To be more specific, the fundamental light beam L41 and the zero-order light beam L43 are introduced inside the external resonator 20 through the optical mirror 21. The fundamental light beam L31 introduced inside the external resonator 20 is repeatedly reflected by the optical mirrors 21 to 24 in order. This causes the fundamental light beam L31 to resonate. Thus, an intensity of the fundamental light beam L31 can be improved.

On the other hand, the zero-order light beam L43 introduced inside the external resonator 20 passes through the optical mirror 22. Therefore, the zero-order light beam L43 will not resonate. As described so far, in the external resonator 20, only the fundamental light beam L41, which has a wavelength longer than that of the fundamental light beam L31, resonates and is enhanced.

The nonlinear optical crystal 5 is disposed in an optical path between the optical mirrors 21 and 22. The nonlinear optical crystal 5 is a CLBO (CsLiB$_6$O$_{10}$) crystal and generates a sum-frequency of the fundamental light beam L41 and the zero-order light beam L43. The sum-frequency generated in the nonlinear optical crystal 5 becomes the wavelength converted light beam L44 and enters the optical mirror 22. Note that the optical mirror 22 may be a dichroic mirror that transmits the wavelength converted light beam L44 and the zero-order light beam L43 and reflects the fundamental light beam L41.

Then, the wavelength converted light beam L45 that has transmitted the optical mirror 22 is reflected by mirrors 7a and 7b and enters the sampling mirror 8. The sampling mirror 8 is a beam splitter that splits the wavelength converted light beam L45 into wavelength converted light beams L46 and L47. The wavelength converted light beam L46 that has passed through the sampling mirror 8 will be an output light beam. The wavelength converted light beam L47 is reflected by the sampling mirror 8 and detected by the detector 9.

With such a configuration, an output of the wavelength converted light beam L46 with a wavelength of 193 nm can be controlled in a manner similar to that in the third exemplary embodiment. It is thus possible to achieve the same advantage as that described above. Further, in this exemplary embodiment, in the configuration that generates wavelength converted light beams by the single resonant oscillation sum-frequency mixing, the AO modulator 2 is disposed in the optical path of one of the fundamental light beams, which is the fundamental light beam L32. To be more specific, the light beam that does not resonate in the external resonator 20 between the two light beams introduced inside the external resonator 20 is controlled by the AO modulator 2. The intensity of the fundamental light beam L31 easily fluctuates due to the resonance in the external resonator 20. Accordingly, in this exemplary embodiment, the AO modulator 2 is disposed in the optical path of the fundamental light beam L32 that is more stable than the fundamental light beam L31. By doing so, the output of the wavelength converted light beam L46 can be stabilized.

Fifth Exemplary Embodiment

Figure 8:
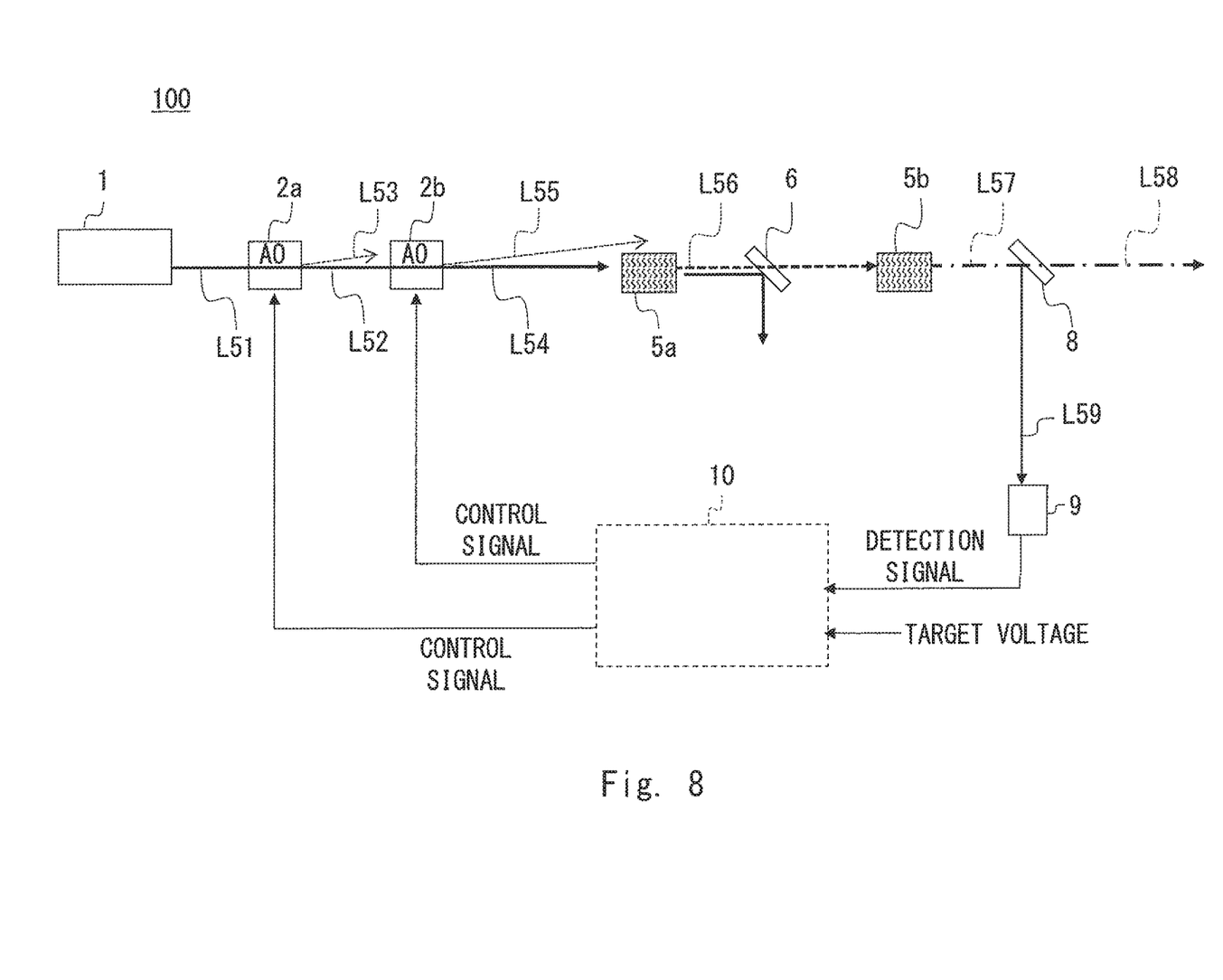
FIG. 8 is a drawing showing a configuration of a light source apparatus according to a fifth exemplary embodiment.

A configuration of a light source apparatus 100 according to a fifth exemplary embodiment will be described by referring to FIG. 8. FIG. 8 is a drawing showing a configuration of the light source apparatus 100. A configuration according to the fifth exemplary embodiment is the same as the configuration according to the first exemplary embodiment except that there are two stages of the AO modulators 2 in the configuration according to the fifth exemplary embodiment. That is, two AO modulators 2a and 2b are arranged between the laser light source 1 and the nonlinear optical crystal 5a.

A fundamental light beam L51 from the laser light source 1 enters the AO modulator 2a. A zero-order light beam L52 of the AO modulator 2a enters the AO modulator 2b. Note that the AO modulator 2a is disposed in such a way that a first-order diffracted light beam L53 of the AO modulator 2a will not enter the AO modulator 2b. A zero-order light beam L54 of the AO modulator 2b enters the nonlinear optical crystal 5a. The AO modulator 2b is disposed in such a way that a first-order diffracted light beam L55 of the AO modulator 2b will not enter the AO modulator 2b.

In a manner similar to that of the first exemplary embodiment, two nonlinear optical crystals 5a and 5b are arranged in the subsequent stages of the AO modulator 2b. Thus, the zero-order diffracted light beam L54 from the AO modulator 2b enters the nonlinear optical crystal 5a. In a manner similar to that of the first exemplary embodiment, the nonlinear optical crystal 5a generates a second harmonic laser beam of the zero-order light beam L54 as a wavelength converted light beam L56. The wavelength converted light beam L56 enters the dichroic mirror 6. The dichroic mirror 6 separates the wavelength converted light beam L56 from a residual fundamental light beam. The wavelength converted light beam L56 that has passed through the dichroic mirror 6 enters the nonlinear optical crystal 5b. The nonlinear optical crystal 5b generates a second harmonic laser beam of the wavelength converted light L56 as a wavelength converted light beam L57.

The wavelength converted light beam L57 enters the sampling mirror 8. The sampling mirror 8 reflects a portion of the wavelength converted light beam L57 so that it will travel in a direction toward the detector 9. A wavelength converted light beam L58 that has passed through the sampling mirror 8 will be an output light beam. A wavelength converted light beam L59 reflected by the sampling mirror 8 is detected by the detector 9. The detector 9 outputs a detection signal to the controller 10. The controller 10 generates a control signal for controlling the AO modulators 2a and 2b in response to the detection signal. It is thus possible to stabilize an output of the wavelength converted light beam L58 in a manner similar to that in the above exemplary embodiments.

When two AO modulators 2 are arranged as described above, a controllable range of outputs can be increased. It is obvious that three or more AO modulators 2 may be arranged in an optical path. Moreover, the two AO modulators 2 are not necessarily arranged between the laser light source 1 and the nonlinear optical crystal 5a. At least one of the AO modulators 2 may be disposed between the nonlinear optical crystals 5a and 5b.

In the first to fifth exemplary embodiments, the light source apparatus 100 in which a wavelength of a laser beam is reduced using the nonlinear optical crystals is configured to allow a zero-order light beam of the AO modulator 2 to enter the crystals. The wavelength conversion efficiency is changed by adjusting a radio frequency signal intensity to the AO modulator 2. Moreover, a portion of a wavelength converted light beam generated by the nonlinear optical crystal is extracted, and an output is monitored by the detector 9. The controller 10 controls the diffraction efficiency of the AO modulator 2 according to the detection signal from the detector 9. In this way, an intensity of a short wavelength light beam can be adjusted or stabilized at a high speed.

Note that the configurations of the first to fifth exemplary embodiments can be combined as appropriate. For example, like in the configuration of the fifth exemplary embodiment, in the configurations of the second to fourth exemplary embodiments, a plurality of the AO modulators 2 may be arranged.

Sixth Exemplary Embodiment

Figure 9:
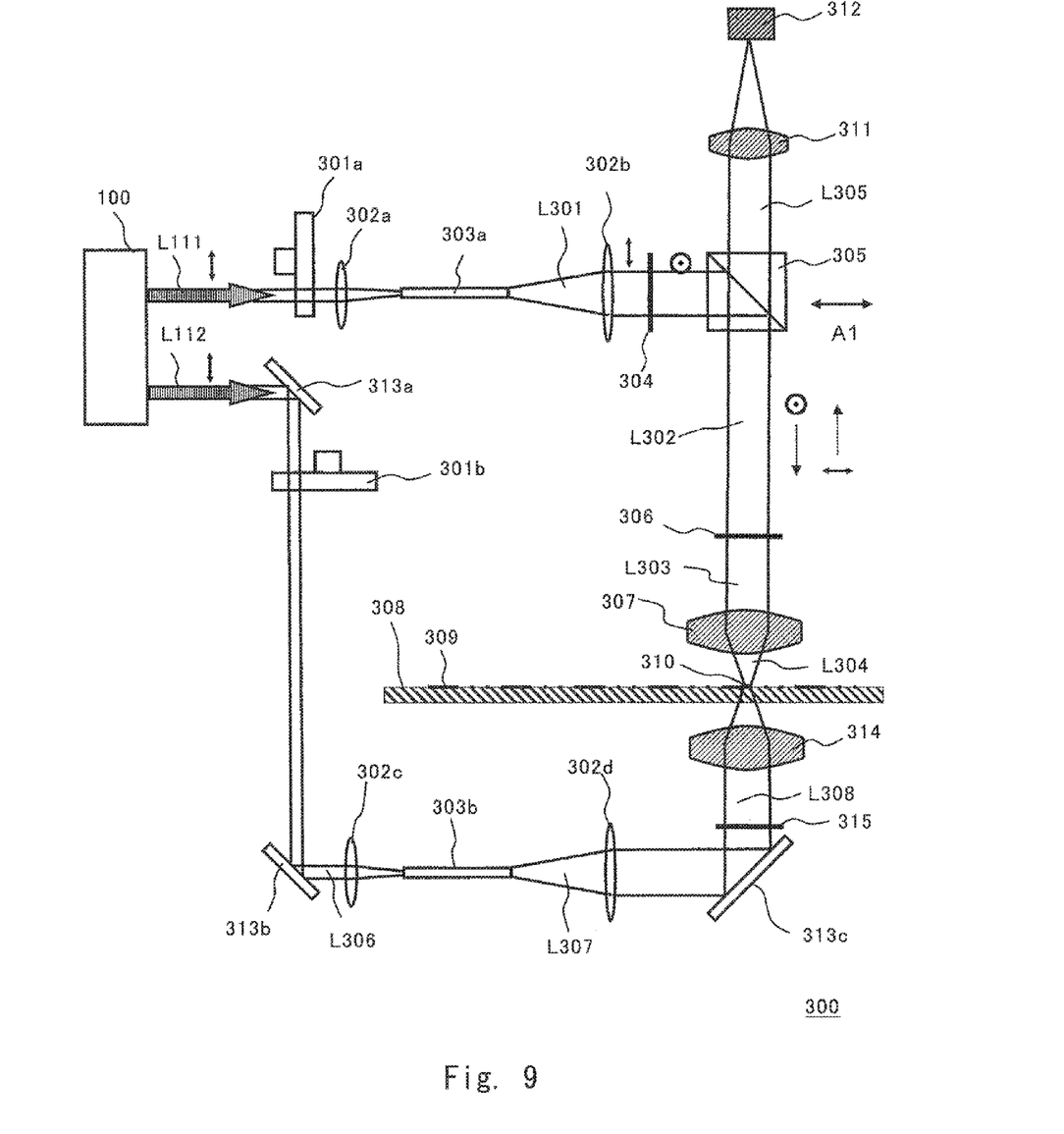
FIG. 9 is a drawing showing a configuration of an inspection apparatus according to a sixth exemplary embodiment.

An inspection apparatus according to a sixth exemplary embodiment is an inspection apparatus that uses the light source apparatus 100 described in the first to fifth exemplary embodiments. An inspection apparatus 300 according to this exemplary embodiment will be described by referring to FIG. 9. FIG. 9 is a drawing showing an overall configuration of a mask inspection apparatus. The inspection apparatus shown in FIG. 9 is an inspection apparatus for masks that are used in an exposure process in manufacturing semiconductors. Note that photomasks which will be inspected are used for lithography that uses DUV light beams with a wavelength of 193 nm in exposure.

As shown in FIG. 9, the mask inspection apparatus 300 includes the light source apparatus 100, lenses 302a to 302d, uniformizing optical systems 303a and 303b, a λ/2 wave plate 304, a polarizing beam splitter 305, a λ/4 wave plate 306, an objective lens 307, an imaging lens 311, a two-dimensional photodetector 312, mirrors 313a to 313c, a condenser lens 314, and a 3λ/4 wave plate 315. The light source apparatus 100 generates DUV light beams with a wavelength in a range of 193.2 to 193.6 nm.

The mask inspection apparatus 300 is supplied with two DUV laser beams, which are each a P wave and which are a DUV laser beam for reflective illumination L111 and a DUV laser beam for trans-illumination L112, respectively, from the light source apparatus 100. For example, when a wavelength converted light beam generated in the light source apparatus 100 is split, the DUV laser beam for reflective illumination L111 and the DUV laser beam for trans-illumination L112 can be generated.

The DUV laser beam for reflective illumination L111 and the DUV laser beam for trans-illumination L112 enter spatial coherence degrading means 301a and 301b, respectively.

The spatial coherence degrading means 301a and 301b degrades coherence of the incident wavelength converted light beams L111 and L112 and removes speckles. The spatial coherence degrading means 301a and 301b can be constructed using optical elements, such as a rotating diffusion plate or a diffractive lens element that can be rotated by a motor or the like. It is also possible to use a liquid crystal spatial light modulator or a deformable mirror as the spatial coherence degrading means 301a and 301b.

The DUV laser beam for reflective illumination L111 is focused at the lens 302a and enters the uniformizing optical system 303a. For example, a so-called rod integrator is suitable for the uniformizing optical system 303a.

A DUV laser beam L301, a spatial distribution of a light intensity of which has been uniformized, is emitted from the uniformizing optical system 303a. The DUV laser beam L301 passes through the lens 302b and the λ/2 wave plate 304, so that a direction of polarization is rotated by 90 degrees to become an S wave. Then, the DUV laser beam L301 that has become the S wave enters the polarizing beam splitter 305 and is reflected to travel in a downward direction in FIG. 9 like a DUV laser beam L302. The DUV laser beam L302 passes through the λ/4 wave plate 306 and becomes a circular polarized DUV laser beam L303. The DUV laser light beam L303 passes through the objective lens 307 and illuminates an observation region 310 on a pattern surface 309 of the mask 308. Note that the above light is an illuminating system called reflective illumination. A reflected light beam that is reflected by the pattern surface 309 of the mask 308 and travels upward is a DUV laser beam L304.

On the other hand, the DUV laser beam for trans-illumination L112 that is supplied from the light source apparatus 100 strikes the mirrors 313a and 313b and is folded to become a DUV laser beam L306. The DUV laser beam L306 is focused by the lens 302c and enters the uniformizing optical system 303b. After the light beam travels inside the uniformizing optical system 303b, a DUV laser beam L307, a spatial distribution of a light intensity of which has been uniformized, is emitted. The DUV laser beam L307 passes through the lens 302d, is reflected by the mirror 313c, passes through the 3λ/4 wave plate 315, and becomes a circular polarized DUV laser beam L308. Then, the DUV laser beam L308 passes through the condenser lens 314 and illuminates the observation region 310 on the pattern surface 309 of the mask 308. Note that the above light is an illuminating system called trans-illumination. Transmitted light that passes through the mask 308 and travels upward will become the DUV laser beam L304.

The DUV laser beam L304 that is reflected by the mask 308 or the DUV laser beam L304 that has passed through the mask 308 passes through the objective lens 307 and the λ/4 wave plate 306, and then returns to a linearly polarized light beam. The DUV laser beam L304 that travels upward will become a P wave, a direction of polarization of which being orthogonal to that of the DUV laser beam L302 travelling downward, and then passes through the polarizing beam splitter 305. As a result, the DUV laser beam L304 travels like a DUV laser beam L305 does, passes through the imaging lens 311, and then strikes the two-dimensional photodetector 312. Then, the observation region 310 is magnified and projected on the two-dimensional photodetector 312, and a pattern of the observation region 310 is inspected. Note that a CCD (Charged Coupled Device) sensor, a CMOS (Complementary Metal-Oxide-Semiconductor) sensor, a TDI (Time Delay Integration) sensor, and the like are suitable for the two-dimensional photodetector 312.

In this way, the pattern of the mask 308 can be inspected using a DUV light beam with a wavelength in a range of 193.2 to 193.6 nm that is almost the same as the exposure wavelength. It is therefore possible to accurately inspect the mask. Further, as high-output DUV light beams can be stably illuminated, accurate inspections can be performed in a short time. It is obvious that a configuration of the inspection apparatus and an object to be inspected are not particularly limited. Moreover, light enters the mask 308 via the spatial coherence degrading means 301a that reduces coherence. Thus, speckles can be removed. Note that an object to be inspected is not limited to the mask 308.

According to this exemplary embodiment, in the light source apparatus in which a wavelength of a laser beam is reduced using the nonlinear optical crystals, highly reliable control on light output can be achieved at a low cost. Regarding a light source for inspecting semiconductors, when an amount of light for illuminating an object under inspection fluctuates even by a small amount, variation is generated in measurement data, thereby resulting in an inaccurate inspection result. Long-term output stability is also desired for a light source for inspecting semiconductors. The light source apparatus according to the above exemplary embodiments can stabilize an amount of light of laser beams. Accordingly, stable inspections can be performed by illuminating objects to be inspected with wavelength converted light beams from the light source apparatus.

By using a zero-order light beam, a wavelength converted light output can be changed to be greater than a theoretical value of a wavelength conversion efficiency. The higher a frequency of an RF signal, which is a control signal, the greater a beam profile of a zero-order light beam changes, and thus an efficiency of wavelength conversion is reduced by greater than or equal to the above theoretical value. It is thus assumed that an output of a wavelength converted light can be adjusted to a greater extent. When an intensity of the wavelength converted light beam is monitored, an RF signal intensity is adjusted and then stabilized in order to obtain a necessary output, a wavelength converted light beam that is stable in a wide range can be obtained.

Note that a detector for monitoring an intensity of a wavelength converted light beam may be disposed in the subsequent stage of the spatial coherence degrading means 301a and 301b. This enables a fluctuation in an output due to the spatial coherence degrading means to be corrected and stabilized light to be used as illumination light.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

The invention claimed is:

1. A light source apparatus comprising:
a first laser light source that generates a first fundamental light beam;
a second laser light source that generates a second fundamental light beam, the second fundamental light beam having a wavelength different from that of the first fundamental light beam;
an at least one nonlinear optical crystal that generates a wavelength converted light beam by sum-frequency mixing, the sum frequency mixing using the first fundamental light beam and a harmonic light beam of the second fundamental light beam as incident light beams;
a detector that detects the wavelength converted light beam;
an acousto-optic modulator that is disposed in an optical path between the first laser light source and the nonlinear optical crystal or an optical path between the second laser light source and the nonlinear optical crystal, the acousto-optic modulator being disposed in such a way that a zero-order light beam enters the nonlinear optical crystal;
a coupling mirror that is disposed in an optical path between the acousto-optic modulator and the nonlinear optical crystal and is disposed in such a way that the harmonic laser beam of the second fundamental light beam will become coaxial with the first fundamental light beam; and
a controller configured to output a control signal that changes a diffraction efficiency of the acousto-optic modulator and to control an output intensity of the wavelength converted light beam according to a detection signal from the detector.

2. The light source apparatus according to claim 1, wherein:
a wavelength of the first fundamental light beam is in a range of 1000 to 1200 nm,
an incident light beam with a wavelength in a range of 200 to 280 nm by fourth-order or fifth-order harmonic generation of the second fundamental light beam enters the nonlinear optical crystal, and
the acousto-optic modulator is disposed in an optical path of the first fundamental light beam.

3. The light source apparatus according to claim 1, wherein:
a wavelength of the first fundamental light beam is in a range of 1000 to 1200 nm,
an incident light beam with a wavelength in a range of 200 to 280 nm by fourth-order or fifth-order harmonic generation of the second fundamental light beam enters the nonlinear optical crystal, and
the acousto-optic modulator is disposed in an optical path of the second fundamental light beam.

4. The light source apparatus according to claim 1, wherein:
a wavelength of the first fundamental light beam is in a range of 1000 to 1200 nm,
an incident light beam with a wavelength in a range of 200 to 280 nm by fourth-order or fifth-order harmonic generation of the second fundamental light beam enters the nonlinear optical crystal, and
the acousto-optic modulator is disposed in an optical path of a second harmonic laser beam of the second fundamental light beam.

5. An inspection apparatus comprising:
the light source apparatus according to claim 1; and
an optical element configured to reduce coherence in an optical path of the wavelength converted light beam.

6. The inspection apparatus according to claim 5, wherein the detector is configured to detect a wavelength converted light beam output that has passed through the optical element.

* * * * *